United States Patent [19]

Riggs

[11] Patent Number: 4,861,924

[45] Date of Patent: Aug. 29, 1989

[54] 1,3,5-TRINITRO-2,4,6-TRIPICRYLBENZENE

[75] Inventor: Robert S. Riggs, Grand Prairie, Tex.

[73] Assignee: Jet Research Center, Inc., Arlington, Tex.

[21] Appl. No.: 237,610

[22] Filed: Aug. 25, 1988

[51] Int. Cl.$^4$ .............................................. C07C 79/10
[52] U.S. Cl. .................................................. 568/931
[58] Field of Search ................ 568/928, 929, 930, 931

[56] References Cited

U.S. PATENT DOCUMENTS

| | | | |
|---|---|---|---|
| 2,301,206 | 10/1942 | France et al. | 260/613 |
| 2,780,656 | 2/1957 | Toland | 260/645 |
| 3,403,185 | 9/1968 | Nilsson et al. | 260/612 |
| 3,450,778 | 6/1969 | Dacons | 260/645 |
| 3,592,860 | 7/1971 | Dacons | 260/645 |
| 3,755,471 | 8/1973 | Dacons | 260/645 |
| 3,895,055 | 7/1975 | Itatani et al. | 260/479 |
| 4,011,265 | 3/1977 | Dacons et al. | 260/578 |
| 4,250,294 | 2/1981 | Hagel et al. | 528/210 |

OTHER PUBLICATIONS

Los Alamos Scientific Laboratory, High-Temperature Vacuum Thermal Stability Tests of Explosives, 1/75, John F. Baytos, pp. 4-6, 11.
Dacons, DTIC Technical Report, 1966.

Primary Examiner—John F. Terapane
Assistant Examiner—Susan Wolffe
Attorney, Agent, or Firm—Arnold, White & Durkee

[57] ABSTRACT

The compound 1,3,5-trinitro-2,4,6-tripicrylbenzene useful as an explosive.

1 Claim, No Drawings

1,3,5-TRINITRO-2,4,6-TRIPICRYLBENZENE

BACKGROUND OF THE INVENTION

1. Field of the Invention

The present invention relates to secondary explosive aromatic nitro compounds and more particularly to polynitropolyphenyls having heat resistant properties. The improved thermal stability and high initiation sensitivity of the present invention make it particularly suitable for utilization in booster cups and exploding bridge wire (EBW) detonators. The present invention also relates to methods for preparing this compound.

2. Brief Description of the Prior Art

The practical use of secondary explosives requires two important properties: good thermal stability and high initiation sensitivity. The problem in developing secondary explosives has always been the negative correlation between these two properties. When a molecule is constructed in such a way that it is extremely stable in high temperature environments it often proves to be so stable that it resists valid detonation attempts.

In addition to the properties of thermal stability and initiation sensitivity, a secondary explosive must have adequate oxidative potential to result in a detonable material. In the case of polynitropolyphenyls, the compound must have a certain number of nitro groups to meet this threshold of detonability. The ideal compound is one that is thermally stable, has high explosive potential due to the large number of nitro groups in the molecule and has a high but controllable sensitivity to initiation.

Over the years several explosive polynitropolyphenyl compounds have been developed which exhibit in varying degrees the properties of good thermal stability and high initiation sensitivity. Among these are 2, 2', 4, 4', 6, 6'-hexanitrobiphenyl (HNB), 2, 2', 2'', 4, 4', 4'', 6, 6', 6''-nonanitroterphenyl (NONA) (U.S. Pat. No. 3,755,471 to Dacons), 2, 2'', 4, 4', 4'', 6, 6', 6''octanitro-m-terphenyl (ONT) (U.S. Pat. No. 3,592,860 to Dacons), and 2, 2', 2'', 2''', 4, 4', 4'', 4''', 6, 6', 6'', 6'''-dodecanitorquaterphenyl (DODECA) (U.S. Pat. No. 3,450,778 to Dacons). The present invention, 1,3,5-trinitro-2,4,6-tripicrylbenzene (TNTPB) has a higher thermal stability than DODECA or NONA. ONT, which has a thermal stability slightly greater than the present invention, has a greatly reduced sensitivity to initiation and cannot be used in many situations. HNB has good thermal stability but it is a liquid at 260°–300° C. and is of little practical value as a high temperature explosive.

Among the many ways secondary explosives are used is as detonators used for oil well perforation. It is particularly important when perforating a well that the explosive used not decompose at high temperatures because of the high temperatures encountered in the drill hole. The explosive used, however, must also be sensitive enough that detonation can be easily initiated. The present invention fills the need both within the oil and gas industry as well as within other industries for a more thermally stable secondary explosive which can be readily detonated.

SUMMARY OF THE INVENTION

The present invention provides a symmetrical polynitropolyphenyl compound 1,3,5-trinitro-2,4,6-tripicrylbenzene (TNTPB) which is an explosive compound with good thermal stability and high initiation sensitivity. The present invention also provides for methods of manufacturing the compound comprising reacting a trihalotrinitrobenzene with a picrylahalide in the presence of copper dust and suitable organic diluent at a temperature ranging between 150° C. and 190° C.

DESCRIPTION OF THE INVENTION

The compound 1,3,5-trinitro-2,4,6-tripicrylbenzene (TNTPB) of the formula shown below

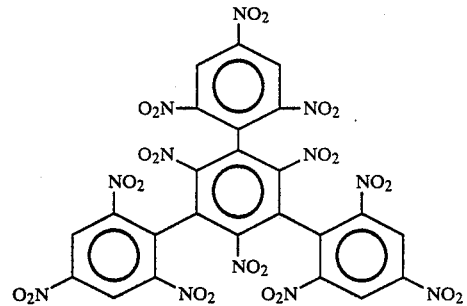

is a secondary explosive with good thermal stability and high initiation sensitivity. One of its immediate applications, although its use is not limited to this, will be as a detonator. Such detonators typically take the form of booster cups or EBW detonators. Both these devices are used in oil well perforation.

TNTPB can be prepared by reacting 1,3,5-trihalo-2,4,6-trinitrobenzene (hereinafter referred to as trihalotrinitrobenzene) with a picrylhalide in the presence of activated copper dust. Theoretically, the halide groups which are selected from the group consisting of bromide, iodide, fluoride and chloride could also be substituted with thiocyanate. The preferred reactants are 1,3,5-trichloro-2,4,6-trinitrobenzene and picrylchloride. The picrylhalide and trihalotrinitrobenzene should be used in stochiometric amounts. The quantity of copper used is mandated by the surface area limitation of the copper being employed. The reaction is generally conducted at a temperature ranging between 150° C. and 190° C. in a suitable organic solvent inert to the reactants, such as nitrobenzene or mesiltylene, which acts as a diluent to control the reaction. After the reaction is complete the product is purified and concentrated by solvent extraction with a suitable solvent, alcohol digestion, and treatment with activated charcoal and treated diatomaceous earth. The product is then recrystallized by evaporation with or without heat.

EXAMPLE

Preparation of TNTPB

The following example illustrates the preparation of TNTPB. In the preferred mode 100 grams of copper powder (Venus Natural Copper 44-f., U.S. Bronze Powder Works) was activated as follows: the copper powder was suspended in 500 mls. of 35% HCl and stirred while heated to 50° C. It was filtered hot and washed three times with 300 mls. of water, one time with 300 mls. of methyl alcohol, and one time with 300 mls. of diethyl ether, and then dried in a vacuum oven. 66 gms. of the copper powder and 200cc of dry mesitylene (Aldrich Chemical) were put into a one liter reaction vessel. 400cc of dry mesitylene, 31.6 grams (.1 moles) of 1,3,5-trichloro-2,4,6-trinitrobenzene (Hercules, Inc., Waco, Tex.) and 74.24 grams (0.3 moles) of picrylchloride (Chemtronics, Swannanoa, N.C.) were added to the addition funnel. The reaction vessel containing the activated copper dust was heated to 160° C. and approximately 20cc of reactants were introduced to the reaction vessel from the addition funnel with stirring.

An induction period of 5 to 10 minutes was required before the reaction began. The induction was considered complete when the copper in the reaction vessel lost its sheen and became bronze colored and then chocolate colored. At that time, the remainder of the reactants were added, with stirring, at a rate such that all of the reactants were added within approximately ten minutes. The reaction was continued at a temperature of 160° C. for a period of time equal to the induction period, approximately 10 minutes.

The mixture was filtered and the inorganic residue was washed first with cold mesitylene to cool the filter cake and then with acetone until the filtrate was nearly colorless. The solvent was removed by steam distillation, the aqueous layer was decanted, and the dark residue was digested in 600 ml. of methanol by refluxing at 65° C. for a period of fifteen minutes. The material was filtered, washed with methanol, and dried in vacuum. The crude product was then dissolved in acetone, treated with 30 gms of activated charcoal and 20 gms of treated diatomaceous earth (Celite ®), and refluxed at 50° C. for 15 minutes.

The suspension was filtered and the filtrate was concentrated by evaporation. At the onset of crystallization the solution was immediately filtered with suction, after which evaporation was continued with application of heat. The major crop of product was collected by filtration when its crystalline product occupied about one-half the apparent volume of the crystal solvent suspension. The product was washed with 100 mls of acetone:-methanol in 1:2 ratio and the liquor was discarded. The yield of material was 19.7 grams (23.2%) and the resulting product did not melt below 400° C.

Analysis of TNTPB

The product was analyzed by the Carlo Erba Elemental Analyzer for carbon, hydrogen and nitrogen. The results are listed in Table 1.

TABLE 1

| Element | Actual Percentage | Theoretical Percentage |
|---|---|---|
| Carbon | 34.06 | 34.06 |
| Hydrogen | 0.78 | 0.71 |
| Nitrogen | 21.09 | 19.86 |
| Oxygen (By Difference) | 44.07 | 45.37 |
| Total | 100.00 | 100.00 |

The product also was analyzed by differential thermal analysis using a DuPont 990 thermal analyzer. The thermagram showed an endotherm (very small) at 40° C. which may have been due to impurity or solvent, an endotherm at 215° C. due to a possible phase change and a very large exotherm at 372° C. due to decomposition.

The infrared spectrum showed absorption peaks at approximately 1345 and approximately 1540 cm$^{-1}$ as is characteristic of nitrated aromatics. It did not show a peak at 1057cm$^{-1}$, the peak normally associated with a chloride on a benezene ring. The $^{13}$C NMR spectrum showed two types of aromatic carbons, ones not bonded to a hydrogen (149.034 ppm, 148.221 ppm, and 147.733 ppm) and ones bonded to a single hydrogen (125.197 ppm, 125.522 ppm).

Comparative Test Data

Thermal stability testing of the present invention was done by comparing the Brisance of several secondary explosives over time at a temperature of 50° F. A 250 mg. sample of test explosive was pressed into a commercially available aluminum cup $\frac{3}{8}$" long ×0.220"ID×0.240" OD under a consolidating pressure of 5000 PSI. The cup containing the test explosive was affixed to a detonating cord which was initiated with a #6 blasting cap. The values reported as percent Brisance in Table 2 below were derived from the depths of dents produced in the aluminum witness plate.

TABLE 2

| INITIATING EXPLOSIVE | PERCENT BRISANCE WITH HOURS AT 500° F. | | | |
|---|---|---|---|---|
| | 100 | 200 | 300 | 400 |
| BTX | 0 | 0 | 0 | 0 |
| ONM | 25 | 0 | 0 | 0 |
| DODECA | 88 | 60 | 0 | 0 |
| NONA | 90 | 84 | 48 | 0 |
| TNTPB | 96 | 90 | 71 | 40 |

Sensitivity testing was done by an adaptation of the conventional card gap test. The test explosive was pressed into an aluminum cup shell as described above and a number of card disks were placed between the test explosive cup and a constant output detonator. The detonating cord affixed to the cup containing the test explosive left an impression on the witness plate if the test explosive detonated. The number of cards through which each test explosive was initiated 50% of the time is shown in Table 3.

TABLE 3

| Test Explosive | 50% Card Gap |
|---|---|
| HNS-II | 12 |
| PYX | 17 |
| TACOT | 13 |
| ONT | 15 |
| DODECA | 30 |
| NONA | 28 |
| TNTPB | 30 |

Application of TNTPB

After the compound is manufactured, two of the ways in which it can be utilized is in booster cups and EBW detonators. One type of booster cup can be prepared by pressing 250 mg. +/−5 mg. of TNTPB into a commercially available aluminum cup 1$\frac{3}{8}$" long ×0.220"ID×0.240" OD under a consolidating pressure of 5000 PSI. An EBW detonator can be prepared by pressing TNTPB into a commercially available EBW detonator in the manner accepted by one skilled in the art. This generally involves pressing the explosive in two increments of different density, with the increment next to the bridge wire, the initial pressing, being pressed at a density less than that of the second increment, the output charge. Both the booster cup and the EBW detonator can then be used for various applications, one of which is oil well perforation.

5
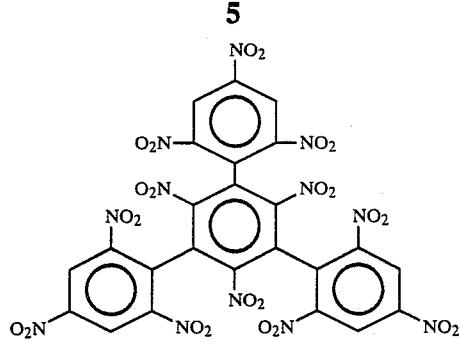
6
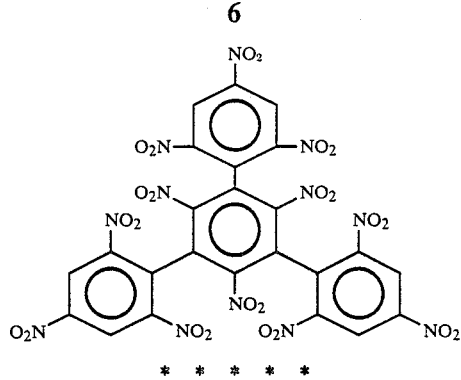

What is claimed is:

1. The compound 1,3,5-trinitro-2,4,6-tripicrylbenzene of the formula